United States Patent [19]

Kydonieus

[11] 4,102,991

[45] Jul. 25, 1978

[54] PROCESS FOR CONTROLLING COCKROACHES AND OTHER CRAWLING INSECTS

[75] Inventor: Agis F. Kydonieus, New York, N.Y.

[73] Assignee: Herculite Protective Fabrics Corporation, New York, N.Y.

[21] Appl. No.: 603,052

[22] Filed: Aug. 8, 1975

[51] Int. Cl.$^2$ .............................................. A01N 17/12
[52] U.S. Cl. ........................................ 424/27; 424/33; 424/78; 424/300
[58] Field of Search ...................... 424/19, 27, 32, 78, 424/300, 33

[56] References Cited

U.S. PATENT DOCUMENTS

| | | | |
|---|---|---|---|
| 2,911,756 | 11/1959 | Geary | 424/84 |
| 3,295,246 | 1/1967 | Landsman et al. | 424/27 |
| 3,852,416 | 12/1974 | Grubb et al. | 424/19 |
| 3,864,468 | 2/1975 | Hyman et al. | 424/27 |

*Primary Examiner*—V. D. Turner
*Attorney, Agent, or Firm*—Sughrue, Rothwell, Mion, Zinn and Macpeak

[57] ABSTRACT

Process for controlling cockroaches and other crawling insects comprising deploying strips of polymeric controlled release dispensers to insect crawl paths and harborages, the dispensers containing a low volatility toxicant for the insects which is made available on the surfaces of the dispensers and which, in a concentration of from 50 to 500 mg/sq.ft. of dispenser active surface area, is lethal to the insects after relatively brief periods of direct physical contact. Generally, strips aggregating from about 1/3 to about 3 sq.ft., of active dispenser surface area are adequate to achieve control of cockroaches and other crawling insects in an average sized room having a floor area of about 100–150 sq.ft.

4 Claims, No Drawings

PROCESS FOR CONTROLLING COCKROACHES AND OTHER CRAWLING INSECTS

BACKGROUND OF THE INVENTION

1. Field of the Invention:

The present invention relates to a process for controlling cockroaches and other crawling insects by the deployment, in insect crawl and harborage areas in residential and commercial buildings, of polymeric controlled release dispensers containing selected toxicants found to have unusually effective knockdown (KD) and kill efficacy for crawling insects based upon fairly short periods of contact between the insect and the dispenser.

2. Description of the Prior Art:

Various species of crawling insects, especially the hard-to-kill cockroach, have been a target for eradication by man for centuries. Lately, pesticides have been developed which have high toxicity for cockroaches, but such pesticides frequently present environmental hazards when used in effective concentrations. The repeated application of low concentrations of available chemical toxicants reduces the danger to the environment but is also less effective and relatively more expensive. Accordingly, attempts have been made to develop methods and products for the controlled release of crawling inset toxicants over extended periods of time in a manner which is relatively less dangerous to man's environment and also is effective to protect the toxicants from premature degradation.

According to the prior art, insect repellent fabrics in the form of tapes or strips have previously been provided which comprise laminated materials at least one layer of which contains an insecticide, alone or in combination with insect baits or attractants. Representative of this prior art are U.S. Pat. No. 2,911,756 — Geary and U.S. Pat. No. 3,295,246 — Landsman et al, although the foregoing references are by no means exhaustive of the prior disclosures concerned with toxicant carriers for pest control. In the Geary patent a flexible sheet or strip is provided with a pressure-sensitive adhesive on one side for mounting the strip on a surface. The other side is provided with an insecticidal and insect attracting composition. An intermediate layer may be provided between the insecticidal composition and the substrate layer, such as cellulose fibers, matted, felted or otherwise joined and bonded to the flexible sheet. When the insecticidal insect attracting compositions are applied to the intermediate layer, the composition is said to be absorbed and kept in close contact therewith. Such devices, of which the Geary structure is typical, have been generally objectionable for a number of reasons, including, (1) the external availability on the exposed surface of the dispenser of the main concentration of toxicant, (2) the lack of protection of the toxicant from atmospheric conditions which may result in rapid loss of efficiency, (3) the relatively low control over the rate at which the toxicant becomes available to the environment, and (4) the lack of structural protection of the toxicant layer from abrasion or other mechanical attrition.

The structure disclosed in the Landsman et al patent remedies some of the foregoing deficiencies of Geary by providing a protective surface coating on the laminated insect repellent tape. The essential feature of the Landsman et al structure is said to be the provision of an absorbent paper core layer saturated with a residual insecticide. The tape is then coated with a light (thin) resinous solution of vinyl or polyethylene or nylon merely to form a surface without forming a substantial layer on the exterior face of the tape. Such structures, with their fragile outer facings, are subject to rupture with the possible result of rapid loss of the insecticide which is merely absorbed in the absorbent core layer of paper or other porous material and the certain result of external availability of the toxicant. Further, such structures would appear to fail to adequately protect the toxicant from degradation due to atmospheric exposure, and to provide minimal control over rate of release of the toxicant.

The assignee of the present application has also developed a new technology for imparting active properties to the surface of solid, nonporous polymeric substrate materials by a technique which comprises applying to selected solid, non-porous polymeric substrate materials a solid, non-porous layer of a polymeric composition containing selected activating agents capable of migrating from the layer into and throughout the substrate. The migrating agents are incorporated in the layer in an amount sufficient to produce an effective level of activity on the exterior surface of the substrate. The application of the Herculite technology, known in the industry as the HERCON process, to the production of pesticidally active polymeric materials is generally described in U.S. Pat. Nos. 3,705,938, 3,857,934 and 3,864,468. Additionally, the assignee of this application is also the assignee of pending application Ser. No. 535,658 in the names of Henry Von Kohorn and myself which relates to pesticide dispensers also based upon the HERCON technology.

Applicant is also aware of polymeric controlled release dispensers commercially available from the Shell Corporation which have generally been employed to control flying insects. These dispensers comprise a volatile toxicant known as 'dichlorvos' or DDVP, which is released into the surrounding atmosphere and which provides a fumigant action in the treated space. Where the space to be treated is unventilated, satisfactory control of crawling insects may be achieved with such fumigant-action dispensers, but in well ventilated rooms this method of control is less effective. Due to the high volatility of DDVP the dispensers tend to lose their efficacy fairly rapidly and the toxicant odors are bothersome to many people.

The present most widely employed approaches for the control of crawling insects involve the use of sprays which are environmentally or aesthetically generally unacceptable for residential use due to persistent toxicity of materials dangerous to man or animals or unpleasant non-toxicity effects, such as unpleasant odors, staining of surfaces, etc. Additionally, where non-persistent toxicants are employed in sprays, the effective life is short, and therefore expensive and inconvenient reapplications are required to achieve even a minimally acceptable level of control.

Accordingly, an object of the present invention is to provide an effective method for controlling cockroaches and other crawling insects which provides prolonged residual effect, minimizes environmental hazards and prevents premature degradation or loss of the toxicant.

DETAILED DESCRIPTION OF THE INVENTION

The process of this invention comprises controlling cockroaches and other crawling insects in buildings by deploying in the crawl paths and harborages of the cockroaches and other crawling insects polymeric controlled release dispensers containing a non-volatile toxicant in sufficient amount such that the toxicant is present on the surfaces of the dispensers in a concentration of from about 50 to 500 mg/sq.ft., and preferably from about 100 to 350 mg/sq.ft. of dispenser active surface area. A plurality of dispensers are preferably provided which have an aggregate active surface area of from about ⅛ to 3 sq.ft., per average sized room of 100 to 150 sq.ft. The non-volatile toxicant is one capable of killing roaches and other insects after the insects have had direct contact with a dispenser for only relatively short periods of time.

In a preferred embodiment the dispensers are provided in the form of tapes about 1 inch wide and 4 inches long and having a pressure-sensitive adhesive backing. The tapes are deployed by adhesively applying them to known insect crawl paths and harborages and by stuffing the tapes into cracks, crevices, piping holes or other apertures which provide insect ingress or egress.

While any suitable polymeric controlled release dispenser may be employed, a preferred dispenser for use in the process is described in copending application Ser. No. 603,053, filed Aug. 8, 1975 in my name. Typically, the dispensers comprise a layer of barrier material, such as MYLAR or Nylon, having a pressure-sensitive adhesive on one side. On the other surface of the barrier layer there is applied a polymeric layer, e.g., a polyvinyl chloride plastisol layer containing a non-volatile toxicant. Over the plastisol layer there is applied a solid, non-porous polymeric layer e.g., a layer of polyvinyl chloride. The toxicant is present in an amount sufficient to provide a surface concentration, usually of about 50 to 500 mg./sq.ft., which has been found to achieve effective levels of knockdown and kill even upon brief contact with roaches or other crawling insects. In the preferred dispensers, the barrier layer blocks the progress of the toxicant towards the adhesive coated surface of the tape, but molecular migration allows certain toxicants to pass through the outer polyvinyl chloride layer and reach the exposed surface of the tape, thus providing an active surface. During the active life of the dispensers, the amount of toxicant in the body of the tape will be adequate to replace the toxicant depleted from the surface and maintain the surface concentration in the effective desired range of 50 to 500 mg. for extended periods of time.

Other less effective but satisfactory controlled release dispensers for use in this invention comprise strips, tapes and films (or other configurations) of solid, polymeric materials, usually thermoplastics, into which effective amounts of non-volatile toxicants may be blended by milling or other processes and from which the toxicant will be gradually released over an extended period of time.

Non-volatile toxicants suitable for use in the foregoing dispensers include, but are not limited to, chlorpyrifos, diazinon, chlordane, carbaryl, malathion, resmethrin, bioresmethrin, propoxur, fenchlorphos, 2-(1,2-dioxolan-2-yl)phenyl-n-methylcarbamate, 2-21-dimethyl-1,3-benzodioxol-4-ol methylcarbamate and Velcicol's organo phosphate compound Vel-4283.

The amount of active surface area of dispensers necessary to give effective control may, of course, be adjusted, depending on the size of the space, prevailing sanitary conditions, ease of insect access, etc.

In addition to the use of a pressure-sensitive adhesive backing, which is preferred, the dispensers may be deployed in accordance with the invention by any practical means, such as by the use of staples or tacks, by means of clips for pipes, ridges or other non-planar surfaces, by the use of separate adhesive tape materials, etc.

The amounts of toxicant (and attractants which optionally may be employed) are not critical, nor is the thickness of the polymeric layer or layers, in the case of the preferred multi-layer dispenser. Concentrations and material thicknesses will ordinarilly be selected to achieve certain objectives in terms of useful life, flexibility, and other properties such as color, ability to create artificial harborages, etc.

In the case of using multi-layer dispensers, as described above, which include a blocking or barrier function, the barrier layers may be composed of polymers containing blocking plasticizers or may be formed from relatively migration resistant polymers, such as, polyamides and polyesters, e.g., Nylon and MYLAR. The latter materials are not resistant to migration of all active materials as has been disclosed in the issued Herculite patent describing the basic HERCON technology, but they are sufficiently resistant to the preferred toxicants identified above largely to control and direct migration of the toxicants through the desired surface layer.

The preferred multi-layer, polymeric dispensers are tough, flexible laminates of integrally bonded layers and are highly resistant to mechanical destruction which could result in accidental and rapid loss of the active agent to the environment. The multi-layer polymeric controlled release dispensers, as well as the homogeneous extruded polymeric dispensers, may be used in any configuration or as part of any structural assembly suited to maximize efficacy against crawling insects, such as cockroaches. Forms such as adhesive backed sheets or strips and confetti are useful. The material may also be incorporated into loops, shelters, traps or the like. A particularly preferred embodiment of the invention comprises a strip of the laminated material provided with a pressure-sensitive adhesive coating on all or part of one surface to facilitate locating the dispenser in a manner to allow maximum effect against crawling insects, such as cockroaches.

The preferred multi-layer polymeric dispensers for use in the process of this invention have the unique ability to protect active ingredients from degradation, thus prolonging the effective life of the insecticide without increase its persistence in the environment.

More specific aspects of the invention will be appreciated in view of the following examples which at the outset demonstrate the efficacy of the preferred dispensers against roaches, and which then proceed to demonstrate the efficacy of the process of the present invention.

EXAMPLE 1

A sheet of polyvinylchloride film having a thickness of 0.004 inch was coated with a plastisol coating prepared by dispersing 100 parts of polyvinylchloride resin in about 25 parts of dioctylphthalate and then dispersing 120 parts of chlorpyrifos into the 125 parts of plastisol. The plastisol thus prepared was mixed until uniform and the coating was applied to the base sheet of polyvinylchloride in a thickness of about 0.02 inches. The coated polyvinylchloride film was then overlaid with a second sheet of polyvinylchloride also having a thickness of 0.004 inches. The assembled layers were then laminated under suitable conditions of heat and pressure until an integral firmly bonded product was obtained. The laminated structure thus produced contained approximately 30.8% chlorpyrifos insecticide based on the total weight of the laminate.

Additional dispensers were prepared in accordance with the procedure described in Example 1 but replacing the active agent as follows:

| Example 2 | Malathion | 5% |
| Example 3 | Malathion | 33.7% |
| Example 4 | Chlorpyrifos | 5% |
| Example 5 | Chlordane | 5% |
| Example 6 | Chlordane | 20.7% |
| Example 7 | Diazinon | 21.2% |
| Example 8 | Carbaryl | 22.7% |
| Example 9 | Propoxur | 10% |

The testing was performed by the methods developed by J. M. Grayson and H. G. Townsend and described in Pest Control, 30(6), Page 14 (1962) and by J. M. Grayson in Pest Control, February (1970). Two tempered masonite panels, held apart by staples, were placed in the bottom of a one gallon glass jar to provide a hiding place for the insects. The polymeric dispenser was placed on the top of the bottom panel. A sample of 30 female cockroaches was placed in each jar and observations on mortality were then made. In the case of the low concentration (5%) dispensers, the mortality (dead or moribund) was observed after six days; in the case of the high concentration dispensers, mortality was observed at the end of one day, three days and six days. The test with the high concentration dispensers was also repeated after 60 days and 150 days after the date of preparation of the dispensers. The results of this testing are shown in Table 1.

and fifty days of aging are generally better than those obtained after two days of aging. This may be explained by the fact that it takes a period of time, sometimes several days or more, depending on the toxicant, and polymer laminate system for the toxicant to migrate and allow the dispenser to become fully functional. Thus, diazinon, chlorpyrifos and chlordane gave complete kill of normal and diazinon-resistant cockroaches after six days of exposure to the dispensers which had been aged for 60 days. Malathion gave complete kill of normal strain and better kill of diazinon-resistant cockroaches than was the case in the first test. Carbaryl gave the poorest results on the diazinon-resistant strain, but produced complete kill of the normal cockroaches after six days of exposure. The results after 150 days of aging do not show any signs of diminishing effectiveness.

Grayson, in his continuous study (Pest Control, February, 1972) to find chemicals that will be effective as residual applications against resistant and susceptible strains of German roaches used chlorpyrifos, diazinon, chlordane and malathion oil sprays as controls in his experiments. The test method used was the same as described above and the deposit of insecticide on the masonite panels was approximately 150 mg/ft.$^2$ The results obtained by Grayson are shown in Table 2. A comparison of the data in Tables 1 and 2 shows that the present dispensers give superior results, especially after two months of aging.

TABLE 2

Percentage Mortalities at the end of one, three and six days[1] following exposure of female German cockroaches to panels which had been treated with different insecticides and the deposits allowed to age for various periods of time. (Testing done at Blacksburg, Virginia, 1971)

TABLE 1

| Ex. No. | Insecticide | % Active Ingredient | Cockroach Strain | % Mortalities(1) After Specified Time of Aging | | | | | | | | |
|---|---|---|---|---|---|---|---|---|---|---|---|---|
| | | | | 2 days | | | 60 days | | | 150 days | | |
| 4 | chlorpyrifos | 5 | diazinon-r | — | — | 73 | — | — | — | — | — | — |
| | | | Normal | — | — | 100 | — | — | — | — | — | — |
| 1 | | 30.8 | diazonon-r | 100 | 100 | 100 | 100 | 100 | 100 | 100 | 100 | 100 |
| | | | Normal | 100 | 100 | 100 | 100 | 100 | 100 | 100 | 100 | 100 |
| 5 | chlordane | 5 | diazenon-r | — | — | 100 | — | — | — | — | — | — |
| | | | Normal | — | — | 100 | — | — | — | — | — | — |
| 6 | | 20.7 | diazinon-r | 0 | 67 | 74 | 97 | 97 | 100 | 71 | 97 | 100 |
| | | | Normal | 63 | 97 | 97 | 100 | 100 | 100 | 97 | 100 | 100 |
| 2 | malethion | 5 | diazinon-r | — | — | 0 | — | — | — | — | — | — |
| | | | Normal | — | — | 77 | — | — | — | — | — | — |
| 3 | | 33.7 | diazinon-r | 0 | 23 | 53 | 41 | 71 | 90 | 83 | 100 | 100 |
| | | | Normal | 77 | 97 | 97 | 100 | 100 | 100 | 100 | 100 | 100 |
| 7 | diazinon | 21.2 | diazinon-r | 30 | 93 | 100 | 97 | 100 | 100 | 100 | 100 | 100 |
| | | | Normal | 97 | 97 | 100 | 100 | 100 | 100 | 100 | 100 | 100 |
| 8 | carbaryl | 22.7 | diazinon-r | 0 | 0 | 0 | 3 | 3 | 17 | 3 | 10 | 53 |
| | | | Normal | 3 | 13 | 16 | 77 | 100 | 100 | 81 | 93 | 100 |

(1)Under each column the first figure is the percentage mortality at the end of a 1-day exposure period, the second figure is the same for a 3-day exposure period and the third figure is the same for a 6-day period.

After two days of aging and six days of exposure to the dispenser, diazinon killed all of the female German cockroaches in both strains. Malathion also was effective in killing cockroaches in a normal strain, but not in the diazinon-resistant strain. Chlorpyrifos was the most effective of the treatments, as it gave complete kill of cockroaches in both strains at the end of one day of exposure. Chlordane was reasonably effective against the normal strain, but only moderately effective against the diazinon-resistant strain. Carbaryl exhibited little activity against cockroaches in either strain.

The dispensers were then aged and retested. The results, as seen in Table 1, after sixty and one hundred

| Insecticide[2] | Cockroach Strain[3] | Age of Insecticide Deposits (Days) | | | | | |
|---|---|---|---|---|---|---|---|
| | | 2 Days | | | 60 Days | | |
| malathion 3.0% oil-base | diazinon-R | 48 | 92 | 100 | 4 | 18 | 56 |
| | Normal | 97 | 99 | 100 | 44 | 90 | 99 |
| chlorpyrifos 0.5% oil-base | diazinon-R | 56 | 100 | 100 | 0 | 8 | 46 |
| | Normal | 99 | 100 | 100 | 59 | 97 | 99 |
| chlordane 3.0% oil-base | diazinon-R | 52 | 74 | 92 | 14 | 56 | 82 |
| | Normal | 100 | 100 | 100 | 29 | 100 | 100 |
| diazinon | diazinon-R | 82 | 100 | 100 | 4 | 16 | 34 |

-continued

| Insecticide[2] | Cockroach Strain[3] | Age of Insecticide Deposits (Days) | | | | | |
|---|---|---|---|---|---|---|---|
| | | 2 Days | | | 60 Days | | |
| 1.0% oil-base | Normal | 100 | 100 | 100 | 82 | 100 | 100 |

[1]Under each column the first figure is the percentage mortality at the end of a 1-day exposure period, the second is for a 3-day exposure period, and the third figure is for a 6-day exposure period.
[2]All materials were applied on a weight/volume basis. The deposit of insecticide was approximately 150 mg/sq.ft. from 1.0% formulations.
[3]Tests with normal strain were replicated 4 times. Duplicate tests were made with strains resistant to diazinon or malathion, making a total of 4 replicates with resistant strains.

EXAMPLE 10

A synthetic pyrethroid (d-trans resmethrin, also known as bioresmethrin) was incorporated into a dispenser constructed in accordance with Example 1 at a concentration of 12.5% of the total weight and the dispenser was evaluated in sheet as well as ⅛inch confetti form in tests against adult, male German cockroaches. Squares of active sheet dispenser were sealed to the upper surfaces of 3 inches × 3 inches glass plates, with opaque plates mounted 3/16 inch above these surfaces to give the insects a hiding place. These assemblies were then placed in containers with 20–100 adult, male German cockroaches and knockdown and kill counts were made as shown in Table 3. The insects and the opaque covers were removed after 48 hours so the active dispenser was fully exposed to ambient laboratory lights (65 fc), temperature (80° F), and humidity (50% RH) until the next test period. The dispenser was compared with the untreated PVC control and with filter paper surfaces treated with bioresmethrin (12.5% of total wt.). The "confetti" form dispenser (2542 mg) was compared with an equal weight of No. 1 Whatman filter paper containing 12.5% pyrethroid by continuous exposure of adult, German cockroaches to the treated materials in large crystallizing dishes.

The sheet dispenser containing synthetic pyrethroid continued to show good knockdown and kill of the insects after 34 days in the laboratory, while the treated filter paper rapidly decreased in activity to a complete loss of effectiveness at the 15 day test. Similarly, the confetti gave high activity through the 15 day period, with loss of effectiveness at the 29 day reading, but the treated filter paper was active only on the first test day (Table 3).

The sheet and confetti forms of the dispensers of this invention containing the bioresmethrin dramatically extended the residual activity of this light degradable compound.

Table 3

Tests Against Adult, Male German Cockroaches (Hazard Strain) With Dispensers Containing Bioresmethrin*

| Material | Days | Total No. Roaches | Knockdown (%) | | | | | | Dead and Moribund (%) | |
|---|---|---|---|---|---|---|---|---|---|---|
| | | | 15 Min. | 30 Min. | 45 Min. | 60 Min. | 90 Min. | 120 Min. | 24 Hr. | 48 Hr. |
| Sheet Form - (Average of 5 Replicates) | | | | | | | | | | |
| Dispenser with | 1 | 98 | 13 | 17 | 20 | 24 | 24 | 28 | 52 | 79 |
| 12.5% | 8 | 100 | 3 | 15 | 27 | 29 | 32 | 33 | 57 | 74 |
| bioresmethrin | 15 | 98 | 19 | 35 | 52 | 58 | 59 | 59 | 86 | 91 |
| | 29 | 100 | 9 | 23 | 31 | 35 | 37 | 37 | 97 | 100 |
| | 34 | 100 | 3 | 13 | 43 | 48 | 62 | 70 | 94 | 98 |
| PVC Control | 1 | 100 | 0 | 0 | 0 | 0 | 0 | 0 | 1 | 1 |
| Dispenser | 8 | 100 | 0 | 0 | 0 | 0 | 0 | 0 | 0 | 1 |
| (Untreated) | 15 | 100 | 0 | 0 | 0 | 0 | 0 | 0 | 0 | 0 |
| | 29 | 100 | 0 | 0 | 0 | 0 | 0 | 0 | 0 | 14 |
| | 34 | 100 | 0 | 0 | 0 | 0 | 0 | 0 | 0 | 0 |
| Filter Paper | 1 | 99 | 30 | 55 | 69 | 73 | 75 | 74 | 86 | 91 |
| with 12.5% | 8 | 98 | 0 | 1 | 1 | 2 | 13 | 19 | 26 | 37 |
| bioresmethrin | 15 | 100 | 0 | 0 | 0 | 0 | 0 | 0 | 0 | 0 |
| Confetti Form - (Continuous Exposure) | | | | | | | | | | |
| Dispenser with | 1 | 20 | 25 | 90 | 90 | 95 | 95 | 100* | 100 | 100 |
| 12.5% | 8 | 20 | 20 | 75 | 95 | 95 | 100 | 100* | 100 | 100 |
| bioresmethrin | 15 | 19 | 21 | 74 | 84 | 95 | 95 | 95 | 100* | 100 |
| | 29 | 20 | 0 | 0 | 0 | 0 | 0 | 0 | 4 | 13 |
| | 34 | 20 | 0 | 0 | 0 | 0 | 0 | 0 | 0 | 2 |
| Filter Paper | 1 | 20 | 90 | 100 | 100 | 100 | 100 | 100* | 100 | 100 |
| with 12.5% | 8 | 20 | 0 | 0 | 0 | 0 | 0 | 0 | 0 | 5 |
| bioresmethrin | 15 | 20 | 0 | 0 | 0 | 0 | 0 | 0 | 0 | 0 |

*Cockroaches removed to clear containers for remainder of observations

Table 4

Residual evaluation of Herculite fabric dispensers on plywood against normal *Blattella germanica*.
(Dispensers are stapled on plywood for standard exposure method;
2 tests with 10 adult males each;
30-min exposure;
mortality assessed after 48 hrs.)

| Ex. No. | Insecticide | Conc: (%) | Percent Mortality on Treated Fabrics After Indicated Week of Testing[a] | | | | | | | |
|---|---|---|---|---|---|---|---|---|---|---|
| | | | 0[b] | 1 | 2 | 4 | 8 | 40 | 44 | 48 | 52 |
| | | | Residues on Herculite Fabric Dispensers | | | | | | | | |
| 11 | Carbaryl | 22 | 0 | 0 | 0 | 0 | 0 | 0 | 0 | 0 | 0 |
| 12 | Chlordane | 40 | 100 | 100 | 100 | 100 | 100 | 100 | 100 | 100 | 100 |
| 13 | Chlorpyrifos | 27 | 100 | 100 | 100 | 100 | 100 | 100 | 100 | 100 | 100 |
| 14 | Diazinon | 21 | 100 | 100 | 100 | 100 | 100 | 100 | 100 | 100 | 100 |
| 15 | Malathion | 25 | 0 | 0 | 0 | 0 | 0 | 0 | 0 | 0 | 0 |
| 16 | Propoxur | 23 | 100 | 100 | 100 | 100 | 100 | 100 | 100 | 100 | 100 |

[a]No mortality in checks
[b]Aged 2 hrs.

Table 5.

| Exposure Time (seconds) | 5% Propoxur* | | | | | |
|---|---|---|---|---|---|---|
| | % Knockdown, min. After Exposure | | | % Dead, Days After Exposure | | |
| | 20 | 30 | 50 | 1 | 2 | 3 |
| 2 | 30 | 85 | 100 | 0 | 60 | 100 |
| 10 | 50 | 100 | — | 5 | 90 | 100 |
| 30 | 65 | 100 | — | 10 | 95 | 100 |
| 60 | 35 | 100 | — | 10 | 90 | 100 |
| 120 | 60 | 100 | — | 15 | 100 | — |
| 240 | 85 | 100 | — | 20 | 100 | — |
| Control | 0 | 0 | 0 | 0 | 0 | 0 |

*o-isopropoxyphenyl methylcarbamate or 2-(1-methylethoxy)phenol methylcarbamate

EXAMPLE 17

A dispenser was prepared generally in accordance with Example 1, but incorporating about 5% by weight of o-isopropoxyphenyl methyl carbamate (propoxur). Knock down and mortality of adult male German cockroaches were observed after various periods of exposure of the roaches to the dispenser. The results are set forth in Table. 5.

It will be seen from the data in Table 5 that surprisingly high knockdown and mortality rates were realized after extremely brief contact times. For example, after exposure for only two seconds, 100% of the roaches were dead three days after the exposure. As the exposure times were increased from 2 to 240 seconds, however, much faster knockdown rates were observed and 100% mortality was achieved two days after exposure where the exposure span was 120 seconds.

EXAMPLES 18–19

Dispensers were prepared generally in accordance with Example 1 but 10% chlorpyrifos and 9% diazinon respectively, were incorporated in the structure. It will be seen from Tables 6 and 7 that somewhat longer exposure times are required to achieve 100% mortality using these agents in the dispensers of this invention, but significant mortality was observed for each type four days after exposure for two minutes or less.

Table 6

| Exposure Time (Minutes) | 10% Chlorpyrifos | | | | | |
|---|---|---|---|---|---|---|
| | % Knockdown, hrs After Exposure | | | % Dead, Days After Exposure | | |
| | 2 | 4 | 7 | 1 | 2 | 4 |
| 2 | 0 | 0 | 5 | 10 | 30 | 45 |
| 10 | 0 | 0 | 0 | 5 | 10 | 20 |
| 20 | 5 | 65 | 85 | 75 | 100 | — |
| 30 | 0 | 30 | 70 | 65 | 90 | 95 |
| 50 | 5 | 40 | 70 | 85 | 90 | 95 |
| 60 | 0 | 50 | 75 | 80 | 90 | 100 |

Table 7

| Exposure Time (Minutes) | 9% Diazinon | | | | | |
|---|---|---|---|---|---|---|
| | % Knockdown, hrs After Exposure | | | % Dead, Days After Exposure | | |
| | 2 | 4 | 7 | 1 | 2 | 4 |
| 1 | 0 | 0 | 0 | 10 | 15 | 35 |
| 2 | 0 | 35 | 45 | 5 | 55 | 80 |
| 10 | 5 | 35 | 70 | 10 | 100 | — |
| 20 | 10 | 70 | 95 | 20 | 90 | 100 |
| 30 | 50 | 100 | — | 20 | 100 | — |
| 40 | 45 | 85 | 100 | 28 | 100 | — |
| Control | 0 | 0 | 0 | 0 | 0 | 5 |

It is expected that chlorpyrifos, diazinon and the other toxicants used in the present invention also would show knock down and kill after very short exposure of the roach to the dispenser, e.g., on the order of two seconds. Since the other agents are somewhat slower acting than propoxur, however, toxicity results take longer to become evident.

EXAMPLE 20

Dispensers were prepared generally as described in Example 1, but containing 5% by weight of propoxur. The roaches were allowed to come in contact with the dispensers in a cardboard carton situated in a larger container and 75% were knocked down or killed after 10 days. The only roaches not knocked down in these tests were observed resting inside the cardboard carton on the lid, only inches from the dispensers.

In replicates of the foregoing tests the roaches were not permitted contact with the tapes, the hole in the cardboard carton having been closed by taping fine screening over the ½ inch hole. The larger plastic container in which the cardboard box was situated was also covered over. After 10 days only 8.3% of the roaches were knockdown or killed.

The results of the tests as reported in Table 8 show that with this dispenser fumigant action is a minor factor, but a significant knockdown is accomplished by minimal direct physical contact, and 100% kill of adult male German cockroaches is achieved after 2 minutes of direct contact.

Table 8

| Treatment[b] | 5% Propoxur | | | | | |
|---|---|---|---|---|---|---|
| | % Knockdown and Dead After Placement In Choice Container (Days)[a] | | | | | |
| | 1 | 2 | 3 | 4 | 7 | 10 |
| Roaches permitted to contact tape | 61.7 | 66.7 | 68.3 | 70.0 | 73.3 | 75.0 |
| Roaches not permitted to contact tape | 1.7 | 5.0 | 5.0 | 6.7 | 6.7 | 8.3 |
| Check | 0 | 0 | 0 | 0 | 0 | 0 |

[a]Three replicates of 20 adult male German cockroaches
[b]Two 1" × 4" dispenser strips adhered to inside of covered ½ pint cardboard carton with ½" hole cut into side. Carton placed in center of larger plastic container and roaches given choice of entering carton or not.

EXAMPLE 21

Diazinan-containing dispensers of the invention were compared for residual activity with sprays of diazinon producing comparable surface concentrations. Sheets of dispensers containing 5% and 16.6% of diazinon respectively, and made generally in accordance with Example 1, were stapled to 6 inches × 6 inches plywood panels in preparation for bio-assay. Diazinon 4EC formulations (Ciba-Geigy) were diluted in water and sprayed on the unpainted plywood panels to yield comparable deposits of 5% and 16.6% of diazinon on the panels. Ten adult German cockroaches were placed on the panels and held under clear, perforated, one-quart plastic containers to confine the cockroaches over the treated panels. Three replicates were performed with the sprayed panels while the tests with the dispensers of the invention were not replicated. The effectiveness of the dispensers versus sprayed applications were evaluated by taking mortality counts at ½-, 1-, 2-, 4-, 6- and 24-hours. The panels were bio-assayed on a weekly basis. The results are set forth in Table 9.

Table 9
Percent Mortality of Adult German Cockroaches After Exposure to Dispenser Containing Diazinon and Spray Applications of Diazinon

| Weeks Aged | Time of Reading | % Mortality at Indicated Treatment | | | | |
|---|---|---|---|---|---|---|
| | | 5% Diazinon Dispenser | 5% Diazinon Spray | 16.6% Diazinon Dispenser | 16.6% Diazinon Spray | Check |
| 0-week | 30-min. | 0 | 3.0 | 0 | 10.0 | 0 |
| | 1-hr. | 0 | 43.3 | 50.0 | 10.0 | 0 |
| | 2-hr. | 30.0 | 86.0 | 93.3 | 10.0 | 0 |
| | 4-hr. | 100 | 100 | 100 | — | 0 |
| | 6-hr | — | — | — | — | 0 |
| | 24-hr | — | — | — | — | 0 |
| 1-week | 30-min. | 0 | 0 | 0 | 3.0 | 0 |
| | 1-hr. | 0 | 20.0 | 40.0 | 63.3 | 0 |
| | 2-hr. | 50.0 | 93.3 | 80.0 | 100 | 0 |

Table 9-continued
Percent Mortality of Adult German Cockroaches After Exposure to Dispenser Containing Diazinon and Spray Applications of Diazinon

| Weeks Aged | Time of Reading | 5% Diazinon Dispenser | 5% Diazinon Spray | 16.6% Diazinon Dispenser | 16.6% Diazinon Spray | Check |
|---|---|---|---|---|---|---|
| | 4-hr. | 100 | 100 | 100 | — | 0 |
| | 6-hr. | — | — | — | — | 0 |
| | 24-hr. | — | — | — | — | 0 |
| 2-weeks | 30-min. | 20.0 | 0 | 16.6 | 16.6 | 0 |
| | 1-hr | 50.0 | 86.6 | 100 | 96.6 | 0 |
| | 2-hr. | 90.0 | 100 | — | 100 | 0 |
| | 4-hr. | 100 | — | — | — | 16.60 |
| | 6-hr. | — | — | — | — | — |
| | 24-hr. | — | — | — | — | — |
| 3-weeks | 30-min. | 0 | 0 | 0 | 0 | 0 |
| | 1-hr. | 26.6 | 13.3 | 70 | 90 | 0 |
| | 2-hr. | 86.6 | 80.0 | 100 | 100 | 0 |
| | 4-hr. | 100 | 100 | — | — | 43.30 |
| | 6-hr. | — | — | — | — | — |
| | 24-hr. | — | — | — | — | — |
| 4-weeks | 30-min. | 0 | 0 | 0 | 0 | 0 |
| | 1-hr. | 0 | 0 | 0 | 6.0 | 0 |
| | 2-hr. | 70 | 0 | 50 | 86.7 | 0 |
| | 4-hr. | 100 | 60 | 100 | 100 | 30 |
| | 6-hr. | — | 93.3 | — | — | 33 |
| | 24-hr. | — | 100 | — | — | 63 |
| 5-weeks | 30-min. | 0 | 0 | 0 | 0 | 0 |
| | 1-hr. | 0 | 0 | 0 | 0 | 0 |
| | 2-hr. | 20.0 | 3.3 | 30.0 | 6.7 | 0 |
| | 4-hr. | 60.0 | 23.3 | 90.0 | 100 | 0 |
| | 6-hr. | 100 | 53.3 | 100 | — | 3 |
| | 24-hr. | — | 100 | — | — | 53 |
| 6-weeks | 30-min. | 0 | 10 | 0 | 0 | 0 |
| | 1-hr. | 0 | 10 | 0 | 0 | 0 |
| | 2-hr. | 10 | 20 | 0 | 16.7 | 0 |
| | 4-hr. | 100 | 76.7 | 90 | 100 | 26. |
| | 6-hr. | — | 100 | 100 | — | 53. |
| | 24-hr. | — | — | — | — | 76. |
| 7-weeks | 30-min. | 0 | 0 | 0 | 3.3 | 0 |
| | 1-hr. | 0 | 0 | 0 | 10.0 | 0 |
| | 2-hr. | 40.0 | 16.7 | 30.0 | 63.3 | 0 |
| | 4-hr. | 70.0 | 86.7 | 100 | 100 | 3. |
| | 6-hr. | 100 | 100 | — | — | 10. |
| | 24-hr. | — | — | — | — | 10. |
| 8-weeks | 30-min. | 0 | 0 | 0 | 0 | 0 |
| | 1-hr. | 10.0 | 0 | 0 | 3.3 | 0 |
| | 2-hr. | 10.0 | 0 | 0 | 10.0 | 0 |
| | 4-hr. | 70.0 | 26.7 | 70 | 63.3 | 0 |
| | 6-hr. | 100 | 86.7 | 100 | 93.3 | 0 |
| | 24-hr. | — | 100 | — | 100 | 10 |
| 9-weeks | 30-min. | 0 | 0 | 0 | 0 | 0 |
| | 1-hr. | 0 | 0 | 0 | 0 | 0 |
| | 2-hr. | 50.0 | 23.3 | 30.0 | 73.3 | 0 |
| | 4-hr. | 100 | 100 | 100 | 100 | 100 |
| | 6-hr. | — | — | — | — | — |
| | 24-hr. | — | — | — | — | — |
| 10-weeks | 30-min. | 0 | 0 | 0 | 0 | 0 |
| | 1-hr. | 10.0 | 6.6 | 0 | 3.3 | 0 |
| | 2-hr. | 70.0 | 6.6 | 50 | 53.3 | 0 |
| | 4-hr. | 100 | 46.7 | 100 | 100 | 3. |
| | 6-hr. | — | 83.3 | — | — | 23. |
| | 24-hr. | — | 100 | — | — | 36. |
| 11-weeks | 30-min. | 0 | 0 | 0 | 0 | 0 |
| | 1-hr. | 0 | 0 | 0 | 0 | 0 |
| | 2-hr. | 0 | 0 | 0 | 0 | 0 |
| | 4-hr. | 80 | 36.9 | 100 | 100 | 0 |
| | 6-hr. | 100 | 96.7 | — | — | 0 |
| | 24-hr. | — | 100 | — | — | 43. |
| 12-weeks | 30-min. | 0 | 0 | 0 | 0 | 0 |
| | 1-hr. | 0 | 0 | 0 | 0 | 0 |
| | 2-hr. | 10.0 | 0 | 10.0 | 3.3 | 0 |
| | 4-hr. | 40.0 | 6.6 | 90.0 | 76.7 | 0 |
| | 6-hr. | 100 | 50.0 | 100 | 100 | 0 |
| | 24-hr. | — | 100 | — | — | 30 |
| 13-weeks | 30-min. | 0 | 0 | 0 | 0 | 0 |
| | 1-hr. | 0 | 0 | 10.0 | 0 | 0 |
| | 2-hr. | 20.0 | 50.0 | 80.0 | 56.7 | 0 |
| | 4-hr. | 100 | 96.7 | 100 | 100 | 76 |
| | 6-hr. | — | 100 | — | — | 100 |
| | 24-hr. | — | — | — | — | — |
| 14-weeks | 30-min. | 0 | 0 | 0 | 0 | 0 |
| | 1-hr. | 0 | 0 | 0 | 0 | 0 |
| | 2-hr. | 10.0 | 0 | 30.0 | 0 | 0 |
| | 4-hr. | 100 | 43.3 | 100 | 93.3 | 0 |
| | 6-hr. | — | 63.3 | — | 100 | 0 |
| | 24-hr. | — | 100 | — | — | 56 |
| 15-weeks | 30-min. | 0 | 0 | 0 | 0 | 0 |
| | 1-hr. | 0 | 0 | 0 | 0 | 0 |
| | 2-hr. | 0 | 0 | 50.0 | 16.6 | 0 |
| | 4-hr. | 20.0 | 13.3 | 90.0 | 60.0 | 0 |
| | 6-hr. | 100 | 30.0 | 100 | 90.0 | 0 |
| | 24-hr. | — | 100 | — | 100 | 10 |
| 16-weeks | 30-min. | 0 | 0 | 0 | 0 | 0 |
| | 1-hr. | 0 | 0 | 0 | 0 | 0 |
| | 2-hr. | 10.0 | 13.3 | 30.0 | 20.0 | 0 |
| | 4-hr. | 100 | 46.6 | 40.0 | 50.0 | 0 |
| | 6-hr. | — | 46.6 | 100 | 70.0 | 0 |
| | 24-hr. | — | 100 | — | 100 | 23 |
| 17-weeks | 30-min. | 0 | 0 | 0 | 0 | 0 |
| | 1-hr. | 0 | 0 | 0 | 3.3 | 0 |
| | 2-hr. | 10.0 | 0 | 10.0 | 3.3 | 0 |
| | 4-hr. | 50.0 | 0 | 50.0 | 20.0 | 0 |
| | 6-hr. | 90.0 | 33.3 | 100 | 70.0 | 0 |
| | 24-hr. | 100 | 100 | — | 100 | 43 |
| 18-weeks | 30-min. | 0 | 0 | 0 | 0 | 0 |
| | 1-hr. | 0 | 0 | 0 | 0 | 0 |
| | 2-hr. | 0 | 0 | 10.0 | 0 | 0 |
| | 4-hr. | 40.0 | 30.0 | 80.0 | 53.3 | 0 |
| | 6-hr. | 100 | 73.3 | 100 | 100 | 10 |
| | 24-hr. | — | 100 | — | — | 80 |
| 19-weeks | 30-min. | 0 | 0 | 0 | 0 | 0 |
| | 1-hr. | 0 | 0 | 10.0 | 0 | 0 |
| | 2-hr. | 0 | 0 | 20.0 | 0 | 0 |
| | 4-hr. | 30.0 | 6.7 | 90.0 | 40.0 | 0 |
| | 6-hr. | 90.0 | 33.3 | 100 | 96.7 | 0 |
| | 24-hr. | 100 | 100 | — | 100 | 30 |
| 21-weeks | 30-min. | 0 | 0 | 0 | 0 | 0 |
| | 1-hr. | 0 | 0 | 0 | 0 | 0 |
| | 2-hr. | 0 | 0 | 0 | 0 | 0 |
| | 4-hr. | 4.0 | 0 | 100 | 30.0 | 0 |
| | 6-hr. | 100 | 6.7 | — | 86.7 | 0 |
| | 24-hr. | — | 96.6 | — | 100 | 0 |

All of the treated surfaces gave 100% control for 21 weeks, as shown in Table 9, when cockroaches were confined for 24 hours. This is very notable when it is considered that diazinon applied at 1% will give 100% control at 24-hours exposure for only 2 to 4 weeks. The 16.6% containing dispenser was the only treatment to sustain 100% control at 6-hours exposure. The 16.6% diazinon spray treatment gave an average of 95% control at 6-hours exposure, but showed definite signs of a break in activity towards the completion of the test, specifically at about 21 weeks of aging.

As has been demonstrated, the preferred dispensers depend for efficacy on direct contact with the cockroach or other crawling insects, and, therefore, for maximum efficacy in field conditions it is necessary that the dispensers not be repellent to the target species. Choice boxes are devices used by some researchers to detect the repellent nature of chemicals as well as the relative insecticidal efficacy of candidate materials to be used for cockroach control. A choice box consists of a 12 × 12 × 4 inch wooden box with a temperated Masonite floor and a vertical partition dividing the box into two compartments of equal size. A ½-inch diameter hole near the top center of the partition provides passage from one compartment to the other. Transparent panels cover both compartments and an opaque cover is placed over one compartment to keep just the one compartment dark. Food and water are placed in the uncovered or light compartment and the cockroaches are introduced into the light side through a hole in the transparent panel covering the light side. Insecticidal material to be tested is placed only in the dark compartment. A cork in the partition hole is removed 2 or 3 hours after the roaches have been placed in a box and observations are made of the number of live and dead cockroaches in each compartment, normally over a period of up to 30 days.

The rate at which cockroaches will flee the light compartment and enter the dark (treated) side indicates the relative repellency of the treatment. The total percent mortality of the cockroaches in the box usually indicates the insecticidal activity of the test material applied in the dark side.

For tests with the preferred dispensers, the tape was applied only at the floor-wall intersections (19.5 inches of tape per 0.5 ft$^2$). No tape was used in the vertical intersections or on the cover. Twenty adult male German cockroaches were put in each of three choice boxes 18 hours after the tape was applied. Data concerning the mortality of the cockroaches was collected in the test for up to 7 days, at which time there was 97% mortality. The dead cockroaches were then removed from each box, a dark cover was set over each treated compartment and the effectiveness of the tape in the boxes was evaluated in a similar manner after 102, 131, 154, 183 and 258 days of aging under ambient atmospheric conditions. The performance of the aged diazinon tape in terms of total percent mortality produced in the choice boxes is shown in Table 10.

Table 10

Performance of Dispensers Containing About 10% Diazinon in Choice Boxes for Up to 283 Days of Aging at Ambient Atmospheric Conditions

| Age of Dispenser | Total % Mortality Days After Start of Test | | | | | | |
|---|---|---|---|---|---|---|---|
| (Days) | 1 | 2 | 3 | 4 | 5 | 6 | 7 |
| Fresh | 5 | 68 | 85 | 93 | 95 | 97 | 97 |
| 102 | 63 | 93 | 98 | 98 | 98 | 98 | 100 |
| 131 | 92 | 95 | 98 | 98 | 100 | | |
| 154 | 65 | ND[1] | 100 | | | | |
| 183 | 95 | 98 | 100 | | | | |
| 250 | —[1] | —[1] | 100 | | | | |
| 283 | — | — | 100 | | | | |

[1]No data collected.

In another series of tests, conventional commercially available cockroach control spray materials were applied to the dark compartments of choice boxes and were tested after periods of aging up to 85 days. The liquids were prepared in water from diazinon 4E, chlorpyrifos 2E, and propoxur 1E commercial formulations and 3 ml of 1% diazinon, 0.5% chlorpyrifos, or 1% propoxur was applied. Three ml was applied because that is about the amount of material that is applied when sprayed just about to runoff under normal conditions. The deposits were allowed to dry 24 hours at which time the standard choice box evaluations were begun. Tests conducted with the same deposits after 20 and 85 days of aging under ambient atmospheric conditions are also summarized in Table 11.

The performance of the liquid deposits in choice boxes was substantially reduced after 85 days of aging. In fact, satisfactory mortality was not achieved within 10 days with diazinon, chlorpyrifos or propoxur. The multi-layer dispensers, on the other hand, had consistently produced very rapid complete mortality for the duration of the test with aged strips.

Repellency in choice boxes is usually calculated on the basis of the percentage of the live cockroaches which can be found alive in the light side. Since there were no live insects after just a brief period of time in the boxes treated with the dispensers of the invention, a repellency of the material could not be detected. With the liquid residues there were usually 90-100% if the surviving cockroaches in the light (untreated) side of each box whenever data was collected. The high percentage of live cockroaches in the light side of the boxes indicated repellency and therefore, also indicated that the initial high degree of effectiveness of the materials was probably due to the high toxicity of the insecticides which would produce mortality after even brief, momentary encounters with the deposits. As the high degree of toxicity is reduced through aging degradation, some cockroaches learn to avoid lethal contacts with the insecticides.

Table 11

Performance In Choice Boxes Of Various Insecticide Deposits[1] Aged for Up to 85 Days Under Ambient Atmospheric Conditions

| Treatment | Age of Deposit (Days) | Total % KD - Days After Start of Test | | | | | |
|---|---|---|---|---|---|---|---|
| | | 1 | 2 | 5 | 6 | 10 | 18 25 |
| Diazinon, 1% | Fresh | 57 | 98 | 100 | | | |
| " | 20 | 75 | 93 | 98 | 98 | 98 | 98 100 |
| " | 85 | —[2] | 0 | 4 | 4 | 62 | 95 100 |
| Chlorpyrifos, 0.5% | Fresh | 18 | 60 | 98 | 98 | 100 | |
| " | 20 | 80 | 97 | 100 | | | |
| " | 85 | —[2] | 32 | 38 | 58 | 87 | 97 97 |
| Propoxur, 1% | Fresh | 17 | 50 | 83 | 100 | | |
| " | 20 | 80 | 97 | 98 | 98 | 98 | 100 |
| " | 85 | —[2] | 7 | 13 | 18 | 22 | 28 62 |
| Untreated | Fresh | 0 | 0 | 2 | 2 | 2 | 2 —[2] |
| " | 20 | 2 | 3 | 8 | 8 | 17 | 21 26 |
| " | 85 | 2 | 3 | 5 | 5 | 7 | 10 15 |

[1]Applied 3 ml dilute emulsion to the Masonite floor of the dark compartment with a pipette. Brushed deposit overthe substrate with a damp camel hair brush.
[2]No data collected.

In accordance with the invention, polymeric controlled release dispensers containing sufficient amounts of non-volatile, contact-effective toxicants, preferably dispensers as exemplified above, are deployed in structures infested with or apt to be infested with roaches or other crawling insects and specifically in known harborages and crawl paths, e.g., in cracks and crevices around pipes, moldings and the like; on the backs and in the dark corners of appliances, shelves, closets, etc. From about ⅛ to about 3 sq.ft., polymeric, controlled release dispenser material containing a non-volatile, contact-effective toxicant having a surface concentration of toxicant of from about 50 to 500 mg/sq.ft. deployed in an average sized room or space (about 100 – 150 sq.ft.) has been found to provide effective control of roaches and other crawling insects. In this context "control" is meant to imply a significant reduction in crawling insect population, not necessarily eradication which is sometimes impossible to achieve due to sanitary or other conditions.

The following tables summarize field tests using dispensers containing propoxur and diazinon. Data from field tests wherein residual spray treatments were used along (or in a few cases, with a fog) are included for comparison.

The dispensers were 1 inch × 4 inches tapes of PVC/PVC plastisol/MYLAR/pressure-sensitive adhesive construction containing about 5% by weight of toxicant initially introduced in the plastisol layer. The dispensers were adherently applied to harborages and crawl path surfaces and cracks and crevices were also treated by inserting a strip or strips. The quantity of strips applied varied according to the size of the apartment kitchen and other rooms, and also according to the number of cracks, crevices and other cockroach harborages. A greater number of roaches were usually found in test sites with many cracks and crevices. Table 12 comparing the results of HERCON "Roach-Tape" treatments with spray alone shows the control was definitely better when the strips were used. All sprayed test sites were sprayed by commercial pest control operators or by apartment complex employees who regularly handle spraying duties. After 1 to 1½ months, percent reduction in sprayed sites was only 55.86%, while test sites with the strips showed more than 70% reduction. The highest average reduction obtained by spray along was 61.87%, while in the dispenser treated sites it was 92.76%. A reduction of 100% was often observed in dispenser treated sites with moderately low infestations.

Very good control was obtained in test sites with the process of this invention. The reduction after 1 to 1½ months was greatest with dispensers containing propoxur with 88.29% (dispensers of chlorpyrifos had 86.07%, and diazinon containing dispensers had 80.69% reduction). Please note that in the spray along sites, reduction after 1 to 1½ months was only 55.86%. Reduction values in test sites treated with dispensers according to this invention were greater two to five months after strip application.

DEFINITIONS

| | |
|---|---|
| % Reduction | : Percentage of infestation reduction; this is obtained by dividing the number of roaches killed by the total number of roaches observed during the pre-count. |
| Pre-Count or P/C | : This is the number of roaches observed prior to application of insecticidal dispenser strips or application of residual sprays. |
| No. Roaches Killed | : This is estimated by substracting follow-up count from pre-count. |
| Follow-Up Count or F/U | : This is the number of roaches observed after application of strips or spray.<br>1F/U: This indicates the number of roaches observed 1 to 1½ months after strip application (or spray application).<br>2F/U: This indicates the number of roaches observed 2 to 3 months after treatment.<br>3F/U: This indicates the number of roaches observed 3 to 5 months after treatment. |
| 1Red'n | : This is % REDUCTION based on the first follow-up (1F/U) count. |
| 2Red'n | : This is % REDUCTION based on the second follow-up (2F/U) count. |
| 3Red'n | : This is % REDUCTION based on the third follow-up (3F/U) count. |

Note: All estimates of level of infestation, i.e., pre-counts and follow-upcounts, were obtained by using the FLUSHING METHOD. A sub-lethalflush using a pressurized pyrethrin/PBO (aerosol) spray was used. Emerging roaches were counted for 3 minutes after flushing.

Note: All estimates of level of infestation, i.e., pre-counts and follow-up counts, were obtained by using the FLUSHING METHOD. A sublethal flush using a pressurized pyrethrin/PBO (aerosol) spray was used. Emerging roaches were counted for 3 minutes after flushing.

Table 12

| Dispenser Tape Treatments Alone Versus Residual Spray Alone | | | | | |
|---|---|---|---|---|---|
| Average No. Strips Per Site | No. Sites | Average No. Roaches Per Site | % Reduction | | |
| | | | 1 Red'n | 2 Red'n | 3 Red'n |
| 40 or less* | 54 | 16.26 | 71.50 | 92.76 | 91.93 |
| 41 or more | 33 | 75.18 | 84.26 | 86.52 | 79.98 |
| Spray Treatments | 45 | 38.71 | 55.86 | 61.87 | 57.21 |

Dispenser tapes were applied as needed. Fifty-four of 87 test sites which received the dispenser treatment had 40 strips or less. This represents 62.07% of the total tape-treated sites, suggesting that an average apartment can be sufficiently treated with approximately 40 strips. (The presence of more cracks and crevices, and very severe cockroach infestations will also influence the number of strips to be used. The above table also showed that there were approximately 16 cockroaches in sites receiving 40 or less strips, while sites with approximately 75 cockroaches had 41 or more strips. Percentage infestation reduction obtained by using dispenser strips alone was greater than that obtained by using residual sprays.

Table 13

| Dispenser Tapes Containing Propoxur Alone | | | | | | | |
|---|---|---|---|---|---|---|---|
| Summary: | | | | | | | |
| No. sites treated with Propoxur strips alone | | | 25 | | | | |
| Average no. cockroaches per site | | | 66.92 | | | | |
| Averge percentage infestation reduction: | | | | | | | |
| During 1st Follow-Up (after 1 – 1½ mos.) | | | 88.29% | | | | |
| During 2nd Follow-Up (after 2 – 3 mos.) | | | 96.17% | | | | |
| During 3rd Follow-Up (after 3 – 5 mos.) | | | 89.34%* | | | | |

*Obtained from 7 sites

| No. Strips/Site | P/C | 1F/U | 2F/U | 3F/U | 1Red'n | 2Red'n | 3Red'n |
|---|---|---|---|---|---|---|---|
| CALIFORNIA, Alameda | | | | | | | |
| 67 | 30 | 3 | | | 90.00 | | |
| 11 | 35 | 0 | | | 100.00 | | |
| 70 | 130 | 6 | | | 95.38 | | |
| FLORIDA, Orlando | | | | | | | |
| 16 | 8 | 0 | | | 100.00 | | |

Table 13-continued

Dispenser Tapes Containing Propoxur Alone

| | | | | | | |
|---|---|---|---|---|---|---|
| 15 | 1 | 0 | | 100.00 | | |
| 25 | 1 | 0 | | 100.00 | | |
| 25 | 5 | 0 | | 100.00 | | |
| 34 | 3 | 0 | 0 | 100.00 | 100.00 | |
| FLORIDA, Tampa | | | | | | |
| 20 | 5 | 0 | | 100.00 | | |
| 12 | 6 | 0 | | 100.00 | | |
| New York, New York Hotel Site | | | | | | |
| 54 | 20 | 1 | | 95.00 | | |
| 26 | 33 | 4 | | 87.88 | | |
| 34 | 20 | 5 | | 75.00 | | |
| Restaurant Site | | | | | | |
| 82 | 2 | 1 | 0 | 95.00 | 100.00 | |
| NEW YORK, New York Hotel Site | | | | | | |
| 24 | 9 | 1 | 0 | 1 | 88.88 | 100.00 | 88.88 |
| 46 | 100 | — | — | 0 | — | — | 100.00 |
| 40 | 30 | 20 | 0 | 10 | 33.33 | 100.00 | 66.67 |
| 52 | 500 | 200 | 10 | — | 60.00 | 98.00 | — |
| NEW YORK, Candy Factory Site | | | | | | |
| 50 | 50 | 1 | 2 | 98.00 | 96.00 | |

Table 14

Dispensing Tapes Containing Chlorpyrifos Alone

Summary:
No. Sites treated with Chlorpyrifos tapes alone    24
Average no. cockroaches per site    13.17
Average percentage infestation reduction:
  During 1st Follow-Up (after 1 – 1½ mos.)    86.07%
  During 2nd Follow-Up (after 2 – 3 mos.)    100.00%
  During 3rd Follow-Up (after 3 – 5 mos.)    100.00%*

*Obtained from 3 sites

| No. Strips/Site | Cockroach Counts | | | | % Reduction | | |
|---|---|---|---|---|---|---|---|
| | P/C | 1F/U | 2F/U | 3F/U | 1Red'n | 2Red'n | 3Red'n |
| OKLAHOMA, Stillwater | | | | | | | |
| 45 | 35 | 8 | 3 | 3 | 77.14 | 91.43 | 91.43 |
| 45 | 51 | 3 | 8 | 3 | 94.12 | 84.31 | 94.12 |
| 45 | 51 | 8 | 8 | 8 | 84.31 | 84.31 | 84.31 |
| OREGON, Cornelius | | | | | | | |
| 53 | 500 | 75 | 0 | | 85.00 | 100.00 | |
| 40 | 25 | 10 | 0 | | 60.00 | 100.00 | |
| TENNESSEE, Memphis | | | | | | | |
| 28 | 3 | 0 | 0 | 0 | 100.00 | 100.00 | 100.00 |
| CALIFORNIA, Almeda | | | | | | | |
| 14 | 25 | 15 | | | 40.00 | | |
| NEW YORK, New York Hotel Site | | | | | | | |
| 47 | 45 | 0 | | | 100.00 | | |
| 42 | 50 | 0 | | | 100.00 | | |
| 45 | 10 | 0 | | | 100.00 | | |
| Hotel Site | | | | | | | |
| 17 | 3 | 0 | 0 | 0 | 100.00 | 100.00 | 100.00 |
| 11 | 4 | 0 | — | 0 | 100.00 | — | 100.00 |
| 11 | 5 | 3 | — | 0 | 40.00 | — | 100.00 |
| OREGON, Cornelius | | | | | | | |
| 30 | 5 | 5 | 0 | | 0 | 100.00 | |
| TENNESSEE, Memphis | | | | | | | |
| 52 | 25 | 0 | | | 100.00 | | |
| 39 | 23 | 0 | | | 100.00 | | |
| 58 | 30 | 0 | | | 100.00 | | |
| FLORIDA, Orlando | | | | | | | |
| 36 | 2 | 0 | — | | 100.00 | | |
| 36 | 3 | 0 | 0 | | 100.00 | 100.00 | |
| 36 | 5 | 0 | 0 | | 100.00 | 100.00 | |
| 36 | 1 | 0 | 0 | | 100.00 | 100.00 | |
| 36 | 2 | 0 | 0 | | 100.00 | 100.00 | |
| 36 | 7 | 0 | 0 | | 100.00 | 100.00 | |
| 36 | 1 | 0 | 0 | | 100.00 | 100.00 | |
| 36 | 1 | 0 | 0 | | 100.00 | 100.00 | |
| 36 | 3 | 0 | — | | 100.00 | | |
| 36 | 7 | 1 | | | 85.71 | | |
| 36 | 30 | 0 | | | 100.00 | | |
| 36 | 19 | 0 | | | 100.00 | | |
| 36 | 15 | 19 | — | | 0 | — | |

Table 15.

Dispenser Tapes Containing Diazinon Alone

Summary:

Table 15.-continued

Dispenser Tapes Containing Diazinon Alone

| | |
|---|---|
| No. sites treated with diazinon strips alone | 38 |
| Average number of cockroaches per site | 35.92 |
| Average percentage infestation reduction: | |
| During 1st follow-up (after 1 – 1½ mos.) | 80.69% |
| During 2nd follow-up (after 2 – 3 months) | 84.46% |
| During 3rd follow-up (after 3 – 5 months) | 84.74% |

| No. Strips/Site | P/C | 1F/U | 2F/U | 3F/U | 1Red'n | 2Red'n | 3Red'n |
|---|---|---|---|---|---|---|---|
| CALIFORNIA, Alameda | | | | | | | |
| 48 | 35 | 12 | | | 65.71 | | |
| CONNECTICUT, New Haven | | | | | | | |
| 96 | 92 | 36 | 2 | 0 | 60.87 | 97.83 | 100.00 |
| South Orange | | | | | | | |
| 24 | 30 | 1 | 0 | | 96.67 | 100.00 | |
| 37 | 40 | 41 | 20 | | 0 | 50.00 | |
| 36 | 60 | 30 | 50 | | 50.00 | 16.67 | |
| 30 | 30 | 10 | — | | 66.67 | — | |
| FLORIDA, Orlando | | | | | | | |
| 46 | 5 | 0 | 0 | | 100.00 | 100.00 | |
| FLORIDA, Tampa | | | | | | | |
| 95 | 12 | 12 | | | 0 | | |
| 15 | 13 | 0 | | | 100.00 | | |
| 30 | 4 | 0 | | | 100.00 | | |
| 80 | 2 | 0 | | | 100.00 | | |
| GEORGIA, Atlanta | | | | | | | |
| 32 | 63 | 0 | | | 100.00 | | |
| NEW YORK, New York | | | | | | | |
| Hotel Site | | | | | | | |
| 68 | 52 | 6 | | | 88.46 | | |
| 32 | 50 | 5 | | | 90.00 | | |
| 36 | 8 | 0 | | | 100.00 | | |
| Hotel Site | | | | | | | |
| 47 | 150 | 1 | 4 | 5 | 99.33 | 97.33 | 96.67 |
| 15 | 5 | 0 | 0 | 0 | 100.00 | 100.00 | 100.00 |
| 26 | 15 | 3 | 3 | 0 | 80.00 | 80.00 | 100.00 |
| 33 | 20 | 1 | 0 | 2 | 95.00 | 100.00 | 90.00 |
| New Hyde Park | | | | | | | |
| 14 | 10 | 0 | 0 | 5 | 100.00 | 100.00 | 50.00 |
| 30 | 12 | 0 | 0 | 2 | 100.00 | 100.00 | 83.00 |
| Hotel Site | | | | | | | |
| 28 | 5 | 0 | 0 | 0 | 100.00 | 100.00 | 100.00 |
| 22 | 5 | 0 | 0 | 0 | 100.00 | 100.00 | 100.00 |
| 21 | 3 | 0 | 0 | 0 | 100.00 | 100.00 | 100.00 |
| OKLAHOMA, Stillwater | | | | | | | |
| 45 | 35 | 8 | 8 | 3 | 77.14 | 77.14 | 91.43 |
| 45 | 51 | 8 | 8 | 8 | 84.31 | 84.31 | 84.31 |
| 45 | 51 | 8 | 8 | 3 | 84.31 | 84.31 | 94.12 |
| OREGON, Cornelius | | | | | | | |
| 30 | 10 | 5 | 0 | | 50.00 | 100.00 | |
| TENNESSEE, Memphis | | | | | | | |
| 96 | 25 | 7 | 2 | 0 | 72.00 | 92.00 | 100.00 |
| 89 | 7 | 0 | — | 0 | 100.00 | — | 100.00 |
| 36 | 30 | 10 | — | — | 66.67 | — | — |
| 17 | 20 | 5 | 1 | 0 | 75.00 | 95.00 | 100.00 |
| 23 | 100 | 20 | 1 | — | 80.00 | 99.00 | — |
| 73 | 70 | 25 | 45 | 45 | 64.29 | 35.71 | 35.71 |
| 80 | 60 | 45 | 40 | 65 | 25.00 | 33.33 | 0 |
| Public Housing Authority | | | | | | | |
| 118 | 112 | 6 | | | 94.64 | | |
| 60 | 53 | 0 | | | 100.00 | | |
| 43 | 20 | 0 | | | 100.00 | | |

Table 16

Conventional Residual Spray Treatments Alone

| | |
|---|---|
| Summary: | |
| Number of sites receiving spray treatments | 45 |
| Average number of cockroaches per site | 38.71 |
| Average percentage infestation reduction: | |
| During 1st follow-up (after 1 – 1½ mos.) | 55.86% |
| During 2nd follow-up (after 2 – 3 mos.) | 61.87% |
| During 3rd follow-up (after 3 – 5 mos.) | 57.21%. |

| | P/C | 1F/U | 2F/U | 3F/U | 1Red'n | 2Red'n | 3Red'n |
|---|---|---|---|---|---|---|---|
| CALIFORNIA, Alameda | | | | | | | |
| Treatment: Dizainon 4E spray alone | 150 | 11 | | | 92.67 | | |
| CONNECTICUT, New Haven | | | | | | | |
| Treatment: Baygon spray plus fog | 3 | 0 | 0 | 12 | 100.00 | 100.00 | 0 |
| | 90 | 77 | 42 | 62 | 14.44 | 53.33 | 31.11 |
| | 3 | 0 | 0 | 1 | 100.00 | 100.00 | 66.67 |
| | 15 | 1 | 2 | 7 | 93.33 | 86.67 | 53.33 |
| | 55 | 42 | 21 | 60 | 23.64 | 61.82 | 0 |
| | 2 | 0 | 0 | 1 | 100.00 | 100.00 | 50.00 |
| | 80 | 63 | 50 | 12 | 21.25 | 37.50 | 85.00 |

Table 16-continued

Conventional Residual Spray Treatments Alone

| Treatment | | | | | | | |
|---|---|---|---|---|---|---|---|
| Treatment: Diazinon 4E spray plus fog | 5 | 10 | 50 | | 0 | 0 | |
| | 20 | 25 | 1 | | 0 | 95.00 | |
| | 3 | 35 | 19 | | 0 | 0 | |
| | 19 | 0 | 0 | 0 | 100.00 | 100.00 | 100.00 |
| Treatment: Diazinon 4E spray plus fog | 77 | 36 | 0 | 0 | 53.25 | 100.00 | 100.00 |
| | 8 | 2 | 0 | 0 | 75.00 | 100.00 | 100.00 |
| | 32 | 7 | 2 | 28 | 78.13 | 93.75 | 12.50 |
| | 26 | 10 | 5 | — | 61.54 | 80.77 | — |
| | 14 | 4 | 3 | 15 | 71.43 | 78.57 | 0 |
| NEW YORK, New York Hotel Site | | | | | | | |
| Treatment: Diazinon 4E spray alone | 30 | 30 | | | | 0 | |
| | 6 | 4 | 0 | | 33.33 | 100.00 | |
| | 10 | 6 | 4 | | 40.00 | 20.00 | |
| | 30 | 25 | 2 | | 16.67 | 93.33 | |
| Hotel Site | 50 | — | — | 50 | — | — | 0 |
| | 10 | 50 | 1 | — | 0 | 90.00 | — |
| Treatment: Dursban spray biweekly | 8 | 3 | 3 | — | 62.50 | 62.50 | — |
| | 5 | 0 | 0 | — | 100.00 | 100.00 | — |
| | 50 | — | 50 | 75 | — | 0 | 0 |
| Hotel Site | 6 | 5 | 2 | 2 | 16.67 | 66.67 | 66.67 |
| | 10 | 5 | 0 | 0 | 50.00 | 100.00 | 100.00 |
| Treatment: Baygon spray alone | 4 | 19 | 4 | 3 | 0 | 0 | 25.00 |
| OKLAHOMA, Stillwater | | | | | | | |
| Treatment: Diazinon | 51 | 3 | 3 | 8 | 94.12 | 94.12 | 84.31 |
| | 51 | 3 | 3 | 8 | 94.12 | 94.12 | 84.31 |
| | 35 | 3 | 3 | 3 | 94.12 | 94.12 | 94.12 |
| Treatment: Baygon spray alone | 51 | 3 | 3 | 3 | 94.12 | 94.12 | 94.12 |
| | 51 | 3 | 8 | 8 | 94.12 | 84.31 | 84.31 |
| | 51 | 3 | 3 | 8 | 94.12 | 94.12 | 84.31 |
| NEW YORK, New York Hotel Site | 30 | 30 | | | 0 | | |
| Treatment: Diazinon 4E spray alone | 6 | 4 | 0 | | 33.33 | 100.00 | |
| | 10 | 6 | 4 | | 40.00 | 20.00 | |
| | 30 | 25 | 2 | | 16.67 | 93.33 | |
| Hotel Site | 50 | — | — | 50 | — | — | 0 |
| Treatment: Dursaban spray beweekly | 10 | 50 | 1 | — | 0 | 90.00 | — |
| | 8 | 3 | 3 | — | 62.50 | 62.50 | — |
| | 5 | 0 | 0 | — | 100.00 | 100.00 | — |
| | 50 | — | 50 | 75 | — | 0 | 0 |
| Hotel Site | 6 | 5 | 2 | 2 | 16.67 | 66.67 | 66.67 |
| Treatment: Baygon spray alone | 10 | 5 | 0 | 0 | 50.00 | 100.00 | 100.00 |
| | 4 | 19 | 4 | 3 | 0 | 0 | 25.00 |
| OKLAHOMA, Stillwater | | | | | | | |
| Treatment: Diazinon spray alone | 51 | 3 | 3 | 8 | 94.12 | 94.12 | 84.31 |
| | 51 | 3 | 3 | 8 | 94.12 | 94.12 | 84.31 |
| | 35 | 3 | 3 | 3 | 94.12 | 94.12 | 94.12 |
| Treatment: Baygon spray alone | 51 | 3 | 3 | 3 | 94.12 | 94.12 | 94.12 |
| | 51 | 3 | 8 | 8 | 94.12 | 84.31 | 84.31 |
| | 51 | 3 | 3 | 8 | 94.12 | 94.12 | 84.31 |
| Oregon, Cornelius | | | | | | | |
| Treatment: Baygon spray | 350 | 50 | 0 | | 85.71 | 100.00 | |
| TENNESSEE, Memphis Public Housing | | | | | | | |
| Treatment: Diazinon 4E spray alone | 20 | 50 | | | 0 | | |
| | 15 | 30 | | | 0 | | |
| | 100 | 50 | | | 50.00 | | |
| | 35 | 20 | | | 42.86 | | |
| | 10 | 10 | | | 0 | | |
| | 60 | 15 | | | 75.00 | | |
| | 7 | 0 | | | 100.00 | | |

What is claimed is:

1. A process for the control of cockroaches in structures comprising
deploying in the harborages and crawlpaths of the cockroaches a plurality of solid polymeric controlled release dispenser strips consisting essentially of
a barrier layer having on the first side thereof a pressure-sensitive adhesive and on the second side thereof
a polyvinyl chloride plastisol layer containing the insecticide propoxur and on the side thereof opposite said barrier layer,
a polyvinyl chloride layer, wherein
said controlled release is effected by molecular migration of said propoxur through and to the exposed surface of the polyvinyl chloride layer,
said strips have an insecticidally effective surface concentration of propoxur on said exposure surface,
said deploying of the strips is by means of said pressure-sensitive adhesive, and
the cumulative surface area of propoxur bearing surface of the strips is from about ⅛ to about 3 square feet per from about 100 to 150 square feet of floor area of the structure in which control of said cockroaches is sought.

2. The process of claim 1, wherein said barrier layer is a layer of polyethylene terephthalate.

3. The process of claim 1, wherein said barrier layer is a layer of nylon.

4. The process of claim 1, wherein said polyvinyl chloride plastisol layer consists essentially of polyvinylchloride resin, dioctylphthalate and propoxur.

UNITED STATES PATENT OFFICE
CERTIFICATE OF CORRECTION

PATENT NO. : 4,102,991
DATED : July 25, 1978
INVENTOR(S) : Agis F. Kydonieus

It is certified that error appears in the above-identified patent and that said Letters Patent are hereby corrected as shown below:

Column 11, Table 9, line 31 of the data in the table, under "Check" - delete "26." and insert --26.7--

Column 11, Table 9, line 32 of the data in the table, under "Check" - delete "53." and insert --53.3--

Column 11, Table 9, line 33 of the data in the table, under "Check" - delete "76." and insert --76.7--

Column 11, Table 9, line 37 of the data in the table, under "Check" - delete "3." and insert --3.3--

Column 11, Table 9, lines 38 and 39 of the data in the table, under "Check" - delete "10." and insert --10.0--

Column 11, Table 9, line 55 of the data in the table, under "Check" - delete "3." and insert --3.3--

UNITED STATES PATENT OFFICE
CERTIFICATE OF CORRECTION

PATENT NO. : 4,102,991

DATED : July 25, 1978

INVENTOR(S) : Agis F. Kydonieus

It is certified that error appears in the above-identified patent and that said Letters Patent are hereby corrected as shown below:

Column 11, Table 9, line 56 of the data in the table, under "Check" - delete "23." and insert --23.3--

Column 11, Table 9, line 57 of the data in the table, under "Check" - delete "36." and insert --36.7--

Column 11, Table 9, line 63 of the data in the table, under "Check" - delete "43." and insert --43.3--

Column 11, Table 9, line 69 of the data in the table, under "Check" - delete "30" and insert --30.0--

Column 11, Table 9, line 73 of the data in the table, under "Check" - delete "76" and insert --76.7--

Column 11, Table 9, line 81 of the data in the table, under "Check" - delete "56" and insert --56.6--

UNITED STATES PATENT OFFICE
CERTIFICATE OF CORRECTION

PATENT NO. : 4,102,991
DATED : July 25, 1978
INVENTOR(S) : Agis F. Kydonieus

Page 3 of 3

It is certified that error appears in the above-identified patent and that said Letters Patent are hereby corrected as shown below:

Column 12, Table 9, line 4 of the data in the table, under "Check" - delete "10" and insert --10.0--

Column 12, Table 9, line 10 of the data in the table, under "Check" - delete "23" and insert --23.3--

Signed and Sealed this

Twenty-second Day of May 1979

[SEAL]

Attest:

RUTH C. MASON
Attesting Officer

DONALD W. BANNER
Commissioner of Patents and Trademarks